United States Patent
McAllister (10) Patent No.: US 6,190,390 B1
(45) Date of Patent: Feb. 20, 2001

(54) APPARATUS AND METHOD FOR CREATING A DOME TIBIAL OSTEOTOMY

(75) Inventor: Craig M. McAllister, Kirkland, WA (US)

(73) Assignee: Howmedica Osteonics Corp., Allendale, NJ (US)

( * ) Notice: Under 35 U.S.C. 154(b), the term of this patent shall be extended for 0 days.

(21) Appl. No.: 09/429,248

(22) Filed: Oct. 29, 1999

(51) Int. Cl.[7] .................................................. A61B 17/56
(52) U.S. Cl. ............................. 606/87; 606/88; 606/54
(58) Field of Search .................................. 606/87, 54, 55, 606/56, 57, 58, 59, 86, 88, 72, 82, 102; 128/898

(56) References Cited

U.S. PATENT DOCUMENTS

| | | |
|---|---|---|
| 4,409,973 | 10/1983 | Neufeld . |
| 4,632,102 | 12/1986 | Comparetto . |
| 4,952,214 | 8/1990 | Comparetto . |
| 5,049,149 | 9/1991 | Schmidt . |
| 5,569,260 * | 10/1996 | Petersen ........................ 606/87 |
| 5,601,565 | 2/1997 | Huebner . |
| 5,645,548 * | 7/1997 | Augsberger ..................... 606/87 |
| 5,700,267 | 12/1997 | Urbanski . |
| 5,704,941 * | 1/1998 | Jacober et al. .................. 606/88 |
| 6,007,535 * | 12/1999 | Rayhack et al. ................. 606/57 |
| 6,027,504 * | 2/2000 | McGuire ........................ 606/87 |

OTHER PUBLICATIONS

Martin W. Korn, M.D., "A New Approach to Dome High Tibial Osteotomy," *The American Journal of Knee Surgery*, vol. 9, No. 1, Winter, 1996, pp. 13–21.

* cited by examiner

Primary Examiner—Pedro Philogene
(74) Attorney, Agent, or Firm—Arthur Jacob (57) ABSTRACT

An instrument system and a method for creating a dome osteotomy having a semi-cylindrical surface contour configuration with an arcuate profile configuration at a selected location on a proximal tibia utilize a first guide component having a plurality of apertures placed along an arc which follows the arcuate profile configuration of the dome osteotomy and a cannula received in each aperture for establishing an array of parallel drill holes forming a pattern for the surface contour configuration of the dome osteotomy. A second guide component includes a slot which follows the arcuate profile configuration of the dome osteotomy and which is juxtaposed with the array of drill holes to guide osteotomes along the slot and into the tibia to create the surface contour configuration of the dome osteotomy. The osteotomes have a lateral curved configuration for following the arcuate profile configuration and footed osteotomes are used to reach behind the patellar tendon for completing the full dome osteotomy.

13 Claims, 7 Drawing Sheets

APPARATUS AND METHOD FOR CREATING A DOME TIBIAL OSTEOTOMY

BACKGROUND OF THE INVENTION

The present invention relates generally to corrective knee structuring and pertains, more specifically, to apparatus and method for the surgical realignment of the knee through proximal tibial osteotomy.

The surgical management of conditions which result in knee misalignment, one of the most common of which is medial compartment osteoarthritis in the varus knee, includes total knee replacement, unicondylar knee replacement, and proximal tibial osteotomy. While each of these options may be appropriate in particular circumstances, it is preferable, especially in younger patients, to avoid implants and to opt for the less radical procedure of high tibial osteotomy. The most common technique for accomplishing the correction of knee misalignment through high tibial osteotomy currently is wedge osteotomy.

However, problems associated with wedge osteotomy render the procedure difficult to perform, lead to both short-term and long-term complications, and discourage both surgeons and patients from choosing the operation. Wedge osteotomy requires meticulous preoperative calculations and is a technically difficult operation. If the wedge osteotomy is not performed perfectly, a variety of problems can occur. Thus, over-correction and under-correction have been identified as common causes of poor results. Even with ideal correction at the time of surgery, alignment can change with time. Wedge osteotomy creates a mismatch between the bony surfaces of the osteotomy. The proximal side of the wedge is larger in surface area and is composed of primarily softer, cancellous bone, and a thinner metaphyseal cortex, while the distal side has a smaller area, thicker cortices, and less cancellous bone. Such a mismatch creates an abrupt lateral wall and increases the potential for long-term drift. Closing a wedge osteotomy creates other anatomic distortions such as lateral joint line deficiencies, distal joint lines, medial collateral ligament abnormalities, lateral ligament abnormalities, posterior cruciate ligament shortening, and patella infera.

Hence, while proximal realignment is considered to be the procedure of choice for younger patients, and especially those patients with medial compartmental osteoarthritis and varus knees, the early and late complications associated with wedge osteotomy have led many surgeons to avoid proximal tibial osteotomy altogether; however, others have sought alternative methods for achieving a reliable realignment through high tibial osteotomy. Among the most promising of these alternatives is dome osteotomy of the proximal tibia. Dome osteotomy demonstrates significant advantages over wedge osteotomy. Thus, because correction is achieved through a dome, rather than a wedge, there is no significant bone loss and anatomy is preserved. Accurate correction is attained more easily since change can be accomplished intraoperatively, in accordance with the surgeon's judgment, and can be verified in the operating room. The operation is accomplished through an anterior incision, avoiding complications associated with the lateral incision required in wedge osteotomy. The dome osteotomy does not create a significant mismatch between the proximal and distal fragments of the osteotomy. In fact, the relatively large surface area between the fragments promotes early and reliable healing. Since correction is achieved through a dome, both varus and valgus corrections are available. However, to be effective, dome osteotomy requires the reliable creation of an appropriate accurate dome.

SUMMARY OF THE INVENTION

The present invention addresses the creation of an effective dome for dome tibial osteotomy. As such, the present invention attains several objects and advantages, some of which are summarized as follows: Facilitates the accurate creation of a dome osteotomy in a proximal tibia osteotomy for the correction of knee misalignment; assures accuracy in the location and orientation of the dome, as well as in the contour of the dome itself; enables correction of knee misalignment with minimal bone loss in a high tibia osteotomy; allows intraoperative adjustments to attain accurate corrections in accordance with the judgment of the surgeon during the procedure; enables varus or valgus corrections; simplifies the procedure for attaining an accurate dome configuration and orientation; provides increased control for creating a more precise and reliable osteotomy with relative ease and with greater safety; enables the creation of a reliable dome osteotomy more quickly, thereby shortening the duration of the procedure; allows the accomplishment of a precise high tibia osteotomy utilizing an anterior incision and minimal invasiveness; promotes early and reliable healing; provides a reliable alternative to total knee replacement without adversely affecting the ability of the site to receive a total knee replacement, should such a replacement become necessary in the future; reduces the chances for complications experienced in connection with corrections attempted by employing a wedge osteotomy; provides instruments of simplified construction capable of ready use with procedures of minimal complexity for the attainment of exemplary results.

The above objects and advantages, as well as further objects and advantages, are attained by the present invention which may be described briefly as an instrument system for creating a dome osteotomy at a selected location on a proximal tibia, the dome osteotomy having a semi-cylindrical surface contour configuration with an arcuate profile configuration placed at the selected location, the instrument system comprising: a first guide component having a longitudinal length, a lateral width, an altitudinal thickness, and a plurality of apertures extending altitudinally through the first guide component and placed along an arc which follows the arcuate profile configuration of the dome osteotomy, the apertures being aligned essentially parallel to one another and including corresponding central axes extending altitudinally, essentially parallel to one another; a plurality of cannulas, each cannula of the plurality of cannulas having a length greater than the altitudinal thickness of the first guide component, an inside guide surface for receiving a complementary drill and an outside guide surface complementary to a corresponding one of the plurality of apertures for being received within the one aperture for guiding the complementary drill along a drill path aligned with the corresponding central axis of the one aperture; and a first guide component affixation arrangement for affixing the first guide component to the proximal tibia with the arc of the plurality of apertures placed in juxtaposition with the selected location of the arcuate profile configuration; the length of each cannula being great enough to assure that each drill path is located in an array of essentially parallel drill paths, with the array creating a pattern for the surface contour configuration of the dome osteotomy located at the selected location on the proximal tibia.

Further, the present invention includes an osteotome for use in an instrument system for creating a dome osteotomy at a selected location on a proximal tibia, the dome osteotomy having a semi-cylindrical surface contour configuration with an arcuate profile configuration placed at the selected location, the instrument system including a guide component having a slot extending along an arc which follows the arcuate profile configuration of the dome osteotomy, the osteotome having: a longitudinal length for extending through the slot; a lateral curved configuration complementary to the arc of the slot for reception within the slot; and a cutting edge extending along the lateral curved configuration for creating the semi-cylindrical surface contour configuration of the dome osteotomy along the arcuate profile configuration as the osteotome is guided by the slot.

Additionally, the present invention provides an improvement in a method for creating a dome osteotomy at a selected location on a proximal tibia, the dome osteotomy having a semi-cylindrical surface contour configuration with an arcuate profile configuration placed at the selected location, the improvement comprising the steps of: placing a first guide component on the tibia, the first guide component having an altitudinal thickness and a plurality of apertures extending altitudinally through the first guide component and placed along an arc which follows the arcuate profile configuration of the dome osteotomy, the apertures being aligned essentially parallel to one another and including corresponding central axes extending altitudinally, essentially parallel to one another; locating the first guide component so as to juxtapose the arc of the plurality of apertures with the location of the arcuate profile configuration of the dome osteotomy; placing a cannula in each of the plurality of apertures, the cannula having a length greater than the altitudinal thickness of the first guide component, an inside guide surface for receiving a complementary drill and an outside guide surface complementary to a corresponding one of the plurality of apertures for being received within the one aperture for guiding the complementary drill along a drill path aligned with the corresponding central axis of the one aperture; and guiding a complementary drill along each inside guide surface to establish an array of essentially parallel drill holes in the tibia, the array creating a pattern for the surface contour configuration of the dome osteotomy located at the selected location on the proximal tibia.

The invention will be understood more fully, while still further objects and advantages will become apparent in the following detailed description of preferred embodiments of the invention illustrated in the accompanying drawing, in which:

DESCRIPTION OF THE PREFERRED EMBODIMENT

Figure 1:
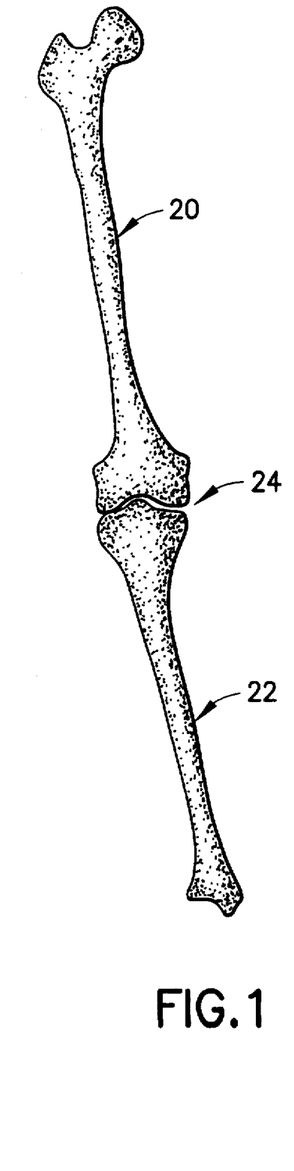
FIG. 1 is a diagrammatic illustration of a femur and a tibia showing knee misalignment arising out of medial compartment osteoarthritis in a varus knee.
Figure 2:
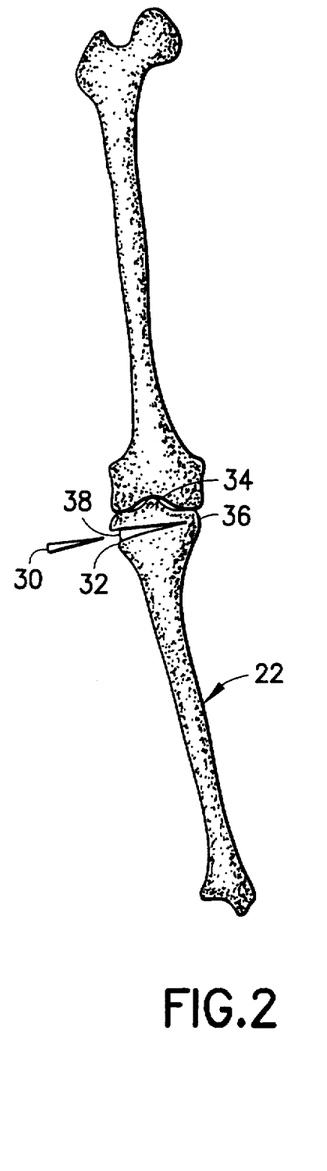
FIG. 2 is a diagrammatic illustration similar to FIG. 1 and illustrating a stage in a correction procedure utilizing a wedge osteotomy.
Figure 3:
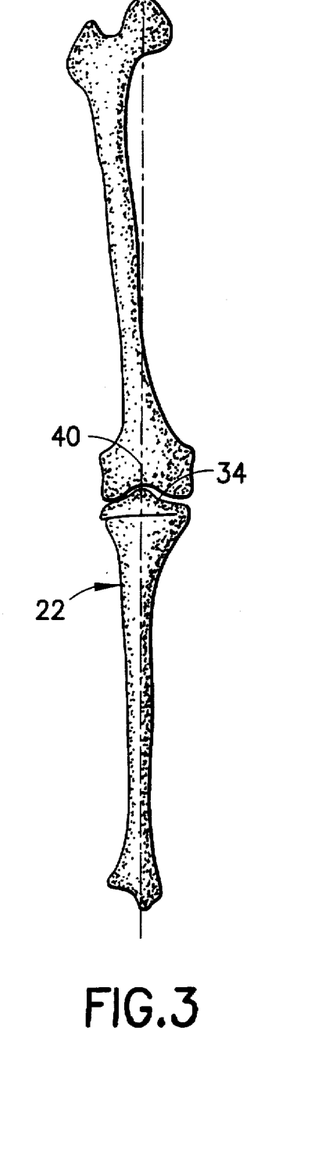
FIG. 3 is a diagrammatic illustration similar to FIG. 2 and showing the correction as attained by the wedge osteotomy.

Referring now to the drawing, a typical misalignment between a femur 20 and a tibia 22 of the leg of a patient is illustrated in FIG. 1, the misalignment being due to a varus knee 24, having occurred as a result of medial compartment osteoarthritis in the knee 24. Correction of the misalignment by utilizing a known method of high tibial wedge osteotomy is illustrated in FIGS. 2 and 3 wherein there is shown the removal of a wedge-shaped portion of bone 30 from the proximal tibia to establish a gap 32 extending transverse to the longitudinal axis of the tibia 22. A proximal fragment 34 remains connected to the proximal tibia at a cortical hinge 36. The gap 32 is wedge-shaped and includes an angle 38 calculated prior to the procedure to accomplish the correction desired. As seen in FIG. 3, correction is attained by closing the gap 32 to rejoin the proximal fragment 34 with the proximal tibia, thereby realigning the tibia 22 to bring the tibia 22 into alignment with the axis 40 of the leg of the patient.

The shortcomings of the use of wedge osteotomy for the correction of misalignment at the knee, as illustrated, are discussed above. It will be seen that the degree of correction is dependent upon careful calculation of the angle 38 of the wedge-shaped gap 32 prior to the procedure, and the surgeon has little opportunity to make corrections during the procedure. Mismatch of the bone at the closed gap 32 can lead to short-term problems in healing, as well as long-term problems, such as drift. Bone is lost due to the necessity to remove the wedge-shaped portion of bone 30. The transverse orientation of the cuts necessary to form the wedge-shaped portion of bone 30 requires a relatively difficult approach through surrounding soft tissue, with the possibility of adverse effects.

Figure 4:
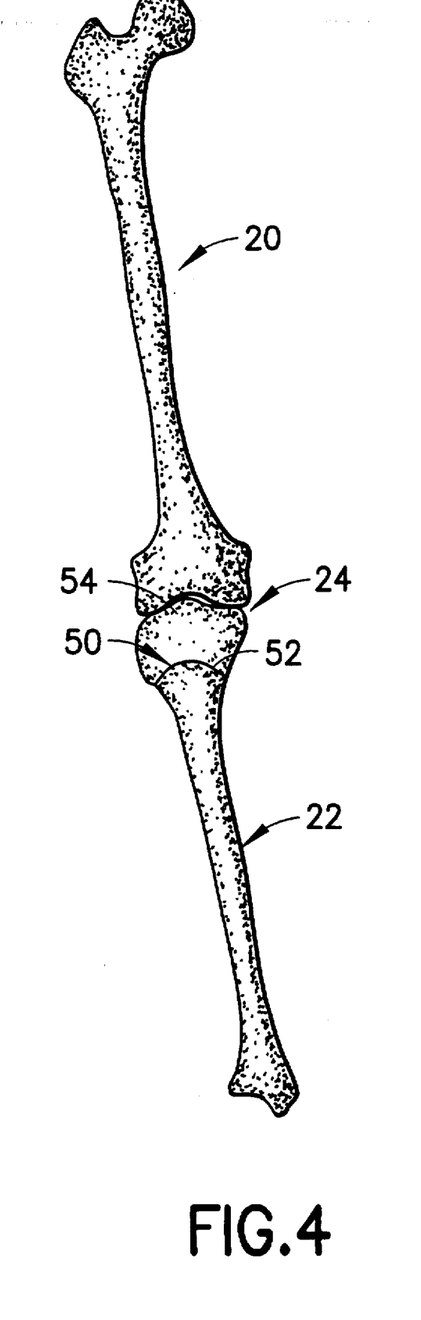
FIG. 4 is a diagrammatic illustration similar to FIG. 2 and illustrating a stage in an alternate correction procedure utilizing a dome osteotomy.
Figure 5:
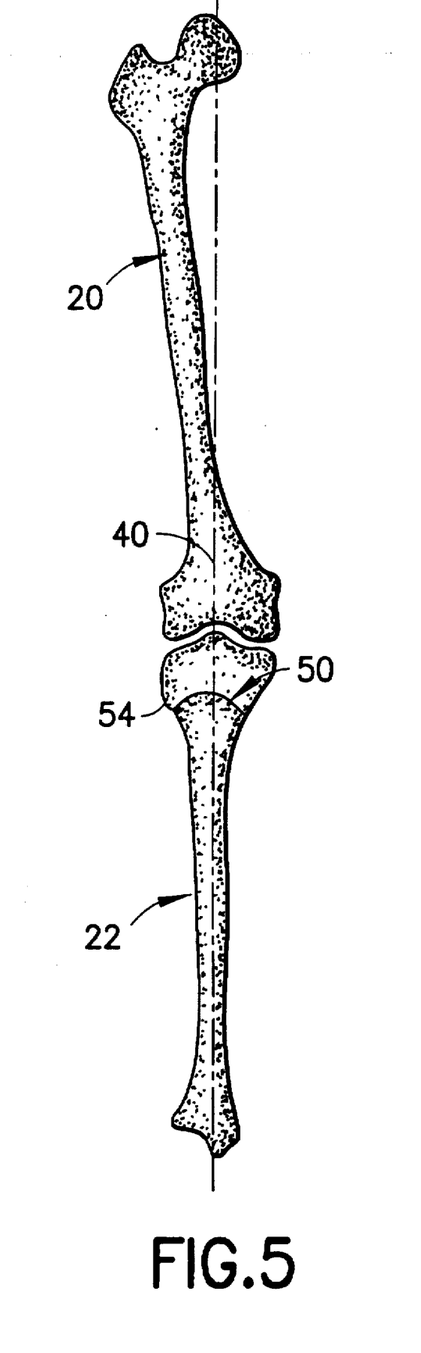
FIG. 5 is a diagrammatic illustration similar to FIG. 3 and showing the correction as attained by the dome osteotomy.

High tibial dome osteotomy provides an alternative for such proximal realignment. As seen in FIGS. 4 and 5, in a dome osteotomy procedure correction is achieved through the creation of a dome 50 at the proximal tibia. The dome 50 has a semi-cylindrical surface contour configuration extending in the anterior-posterior direction, essentially parallel to the joint line of the knee, as illustrated by the arcuate profile configuration 52 of the dome 50. The dome 50 establishes a proximal fragment 54 at the proximal tibia. Correction is attained by rotating the tibia 22 relative to the proximal fragment 54 until the tibia 22 is brought into alignment with the axis 40 of the leg of the patient. The correction is observed and verified during the procedure, and is adjustable intraoperatively in accordance with the judgment of the surgeon, thereby allowing greater latitude for precise alignment as required by the particular conditions encountered at the site of the operation, during the operation. Bone loss is minimized, as is any mismatch upon completion of the correction. The present invention allows the easy, consistent and reliable creation of an accurately placed dome of precise configuration for an effective high tibial dome osteotomy.

Figure 6:
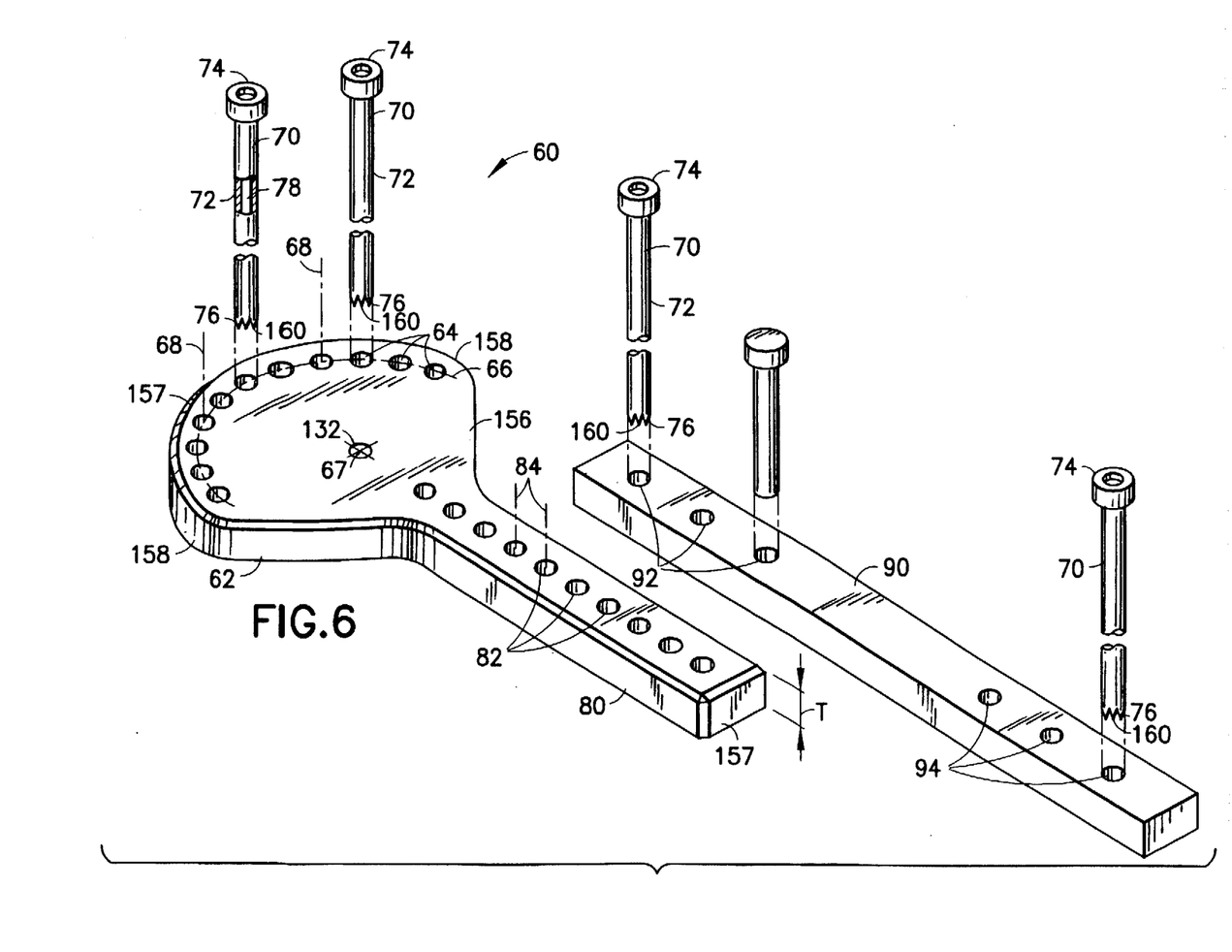
FIG. 6 is a perspective view of drill guide components constructed in accordance with the present invention.

Referring now to FIG. 6, an instrument system 60 constructed in accordance with the present invention includes a first guide component shown in the form of a drill guide 62 having a plurality of apertures 64 placed along an arc 66 located adjacent one end of the drill guide 62, the arc 66 having a center 67 located between the opposite ends of the drill guide 62. Each aperture 64 has a central axis 68 and the central axes 68 of all of the apertures 64 are parallel with one another so that the apertures 64 are parallel. Instrument system 60 includes a plurality of cannulas 70, each cannula 70 having an external guide surface 72 with a diameter complementary to the internal diameter of an aperture 64 so that a cannula 70 can be placed within each aperture 64 with all of the cannulas 70 parallel to one another. Each cannula 70 is cylindrical and includes an upper end 74, a lower end 76, and an internal passage 78 establishing an internal guide surface for receiving a drill and guiding the drill along a drill path parallel to the central axis of the cannula 70. Drill guide 62 includes an arm 80 extending longitudinally adjacent the other end of the drill guide 62, the arm 80 carrying a plurality of openings 82 aligned longitudinally and spaced from one another along the arm 80. Openings 82 include central axes 84 which are parallel to one another and parallel to central axes 68. An extension bar 90 has openings 92 aligned longitudinally along extension bar 90 adjacent a proximal end of the bar 90 and spaced from one another to match the spacing of openings 82 of arm 80. Further openings 94 are placed adjacent a distal end of the bar 90. Openings 92 and 94 have central axes parallel to one another and to central axes 68 and 84.

Figure 7:
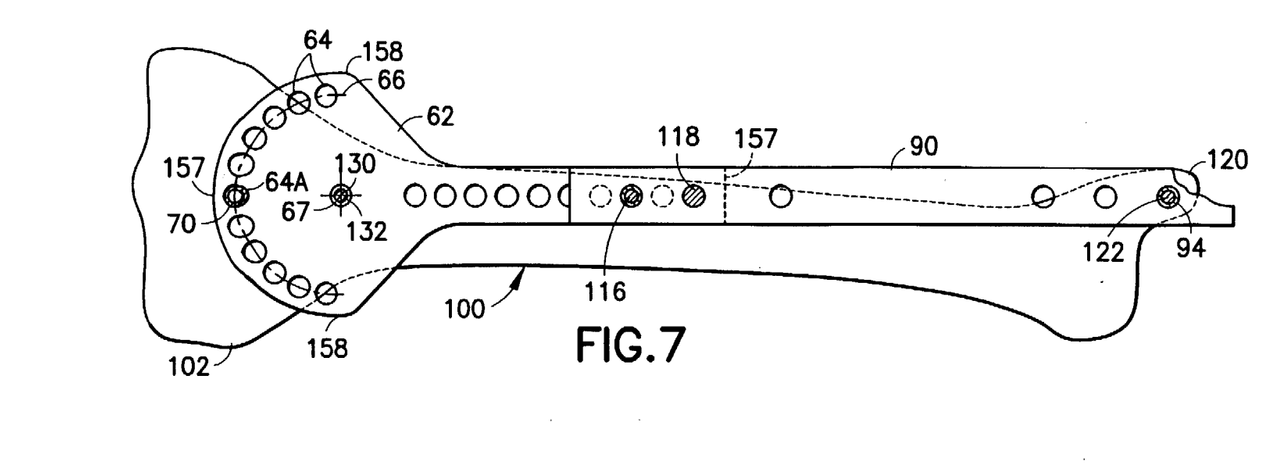
FIG. 7 is a plan view of the drill guide components in place upon a tibia.
Figure 8:
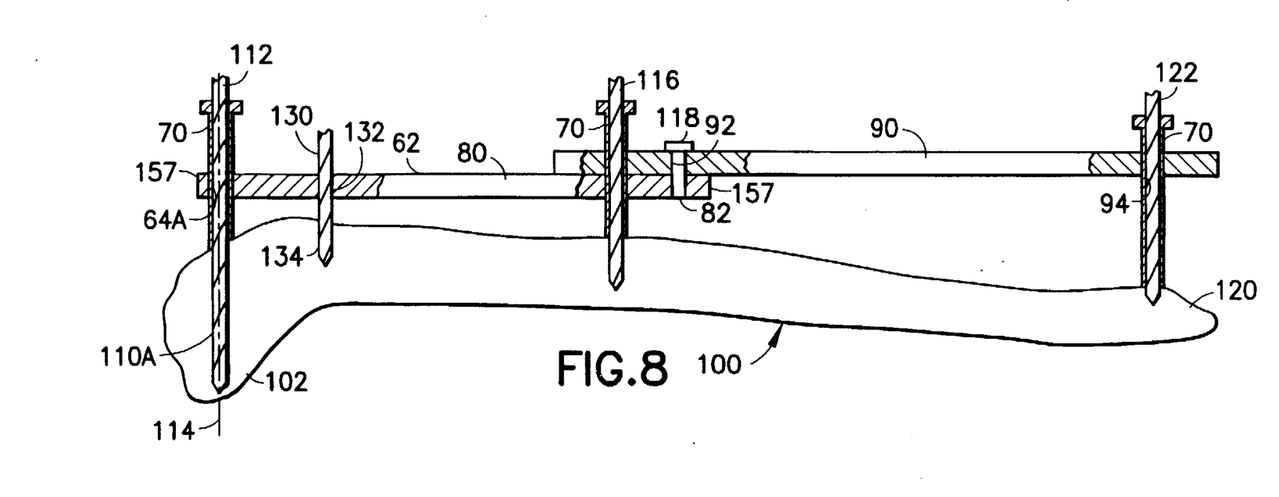
FIG. 8 is an elevational view of the drill guide components in place upon the tibia.
Figures 9, 10:
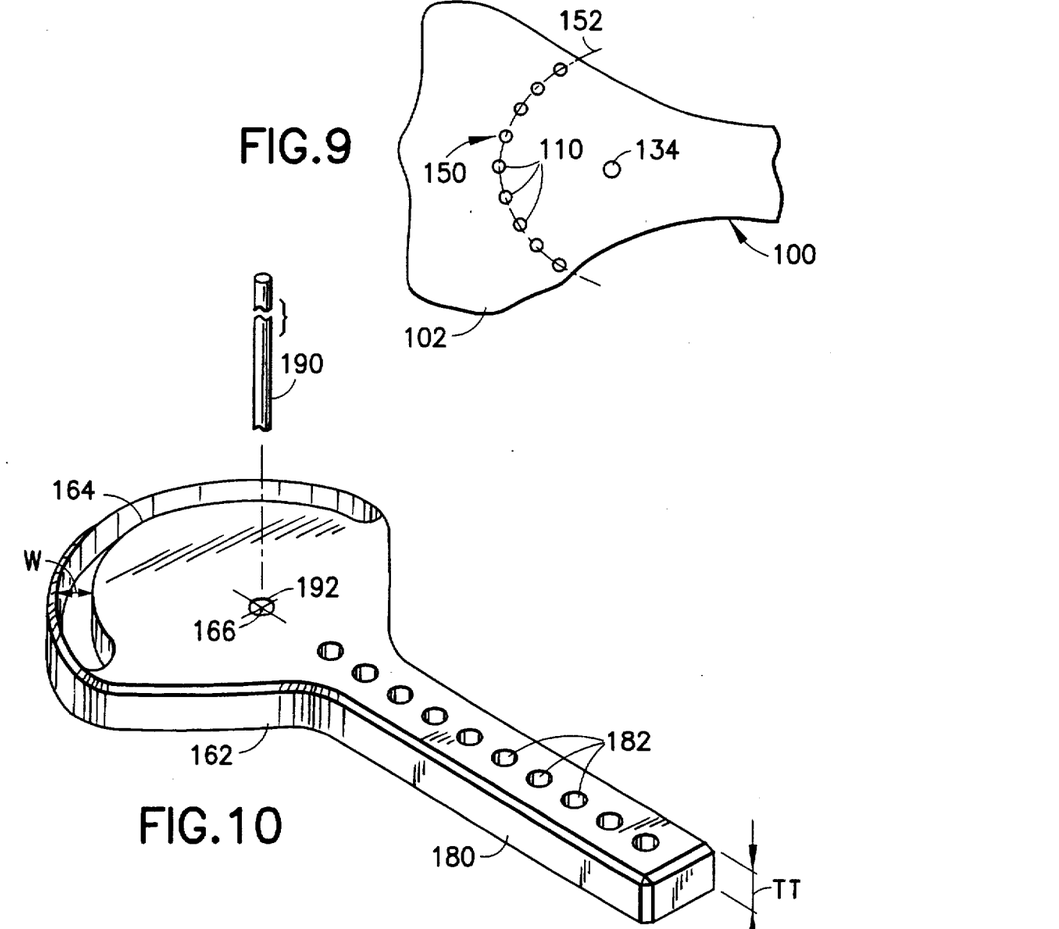
FIG. 9 is a fragmentary plan view of the tibia with the drill guide components removed, after drilling.
FIG. 10 is a perspective view of an osteotome guide constructed in accordance with the present invention.

Turning now to FIGS. 7 and 8, a dome osteotomy is to be created on a tibia 100, at proximal tibia 102, with the apex of the dome osteotomy centered just behind and superior to the patellar tendon insertion on the tibial tubercle. The semi-cylindrical surface contour configuration of the dome osteotomy is to be oriented with a slight posterior slope to match the slope of the joint line of the knee. Such an orientation will maximize the thickness of the proximal fragment and will attain a desired bone-to-bone interface. The arc 66 followed by the plurality of apertures 64 corresponds to the arcuate profile configuration of the semi-cylindrical surface contour configuration of the dome osteotomy, as shown diagrammatically at 52 in FIG. 4, and a first cannula 70 is inserted into the aperture 64A corresponding to the apex of the dome osteotomy. A first drill hole 110A is placed at a location corresponding to the apex of the dome osteotomy by locating the first cannula 70 in accordance with the desired location of the apex of the dome osteotomy and then advancing a drill 112 through the first cannula 70 to establish the drill hole 110A, with the drill hole following the desired drill path 114. The location and orientation of the first drill hole 110A is accomplished with the assistance of fluoroscopy in the lateral plane. With drill 112 thus placed at a location corresponding to the apex of the dome osteotomy, the extension bar 90 is coupled with the arm 80 of the drill guide 62 by means of an anchoring pin 116, guided by a cannula 70, and a coupling pin 118 engaged between aligned openings 82 and 92. The extension bar 90 is placed over the center of the ankle 120 and is secured with a securing pin 122, guided by a cannula 70 inserted into an appropriate opening 94 to align the drill guide 62 with the longitudinal axis of the tibia 100. An anchoring drill 130 then is advanced through a central hole 132 extending through the drill guide 62 at the center 67 of the arc 66, while the extension bar 90 maintains appropriate alignment of the drill guide 62. Subsequently, a cannula 70 is placed within each of the apertures 64 and a drill is advanced through each cannula 70 to establish, along with the first drill hole 110A, a full series 150 of drill holes 110 along a corresponding array of drill paths 114 which follow a profile 152, as seen in FIG. 9, to establish a pattern corresponding to the arcuate profile configuration of the semi-cylindrical surface contour configuration of the dome osteotomy. Should the surgeon deem it necessary or desirable, during the course of the procedure, to shift the position of the plurality of apertures 64 and, hence, the series 150 of drill holes 110, along the established position of the arc 66, either to relocate the series 150 along the location or to provide for additional drill holes 110 along the location, such a shift is accomplished readily by releasing the anchoring pin 1116 and the coupling pin 188, and then rotating the drill guide 62 about the anchoring drill 130.

The use of the cannulas 70 in connection with the parallel apertures 64 in the drill guide 62 allows the drill guide 62 to be constructed in the form of a simple, flat plate-type member 156 extending longitudinally between the opposite first and second ends 157, extending laterally between opposite sides 158, and having only a minimal altitudinal thickness T (see FIG. 6), while the extended length of the cannulas 70 assures that all of the drill holes 110 of the series 150 are parallel with one another and are oriented with the slight posterior slope introduced to match the posterior slope of the joint line. Thus, the construction of member 156 enables not only ease of manufacture, but facilitates handling, placement and accurate location of the drill guide 62 during use, while providing a relatively unobtrusive arrangement of instrumentation during the conduct of the procedure. The extended length of the cannulas 70 then prevents skiving of the drills as the drills are guided and enter the bone of the tibia 100. The combination of drill guide 62 and cannulas 70 allows accurate placement of each drill hole 110 of the series 150 and assures that the drill holes 110 are parallel to one another and extend in an array from anterior to posterior in a coronal arc, the array establishing a pattern for accurately determining the shape of the surface contour configuration of the dome osteotomy and precisely orienting the dome osteotomy at the selected location on the proximal tibia 102. In order to enhance the ability of each cannula 70 to preclude skiving of a drill, the lower end 76 of each cannula 70 includes a toothed configuration 160 which grips the bone of the tibia 100 to deter any skiving movement.

Figure 11:
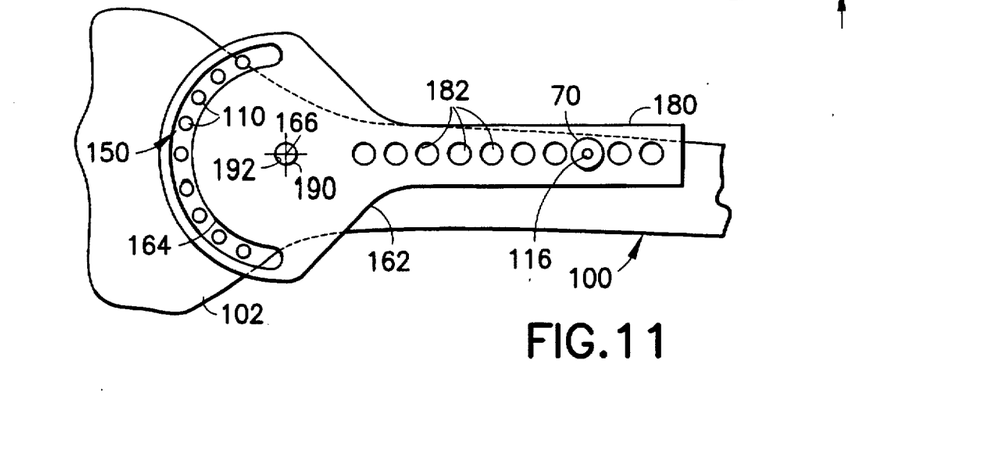
FIG. 11 is a plan view of the osteotome guide in place on the tibia.

The drill guide 62 then is removed and is replaced by a second guide component in the form of an osteotome guide 162, illustrated in FIG. 10. Osteotome guide 162 preferably is constructed in the form of a plate-type member, similar to plate-type member 156, and includes an arcuate slot 164 located adjacent one end of the osteotome guide 162 and passing altitudinally through the thickness TT of the osteotome guide 162. Slot 164 has a width W and an arcuate configuration matching the profile configuration of the dome osteotomy, the arcuate configuration having a center 166 located between the opposite ends of the osteotome guide 162. An affixation arrangement includes an affixation arm 180 extending longitudinally along the osteotome guide 162 adjacent the other end of the osteotome guide 162 and affixation openings 182 placed longitudinally along the affixation arm 180. The osteotome guide 162 is affixed in place upon the tibia 100 by means of a central pin 190 which is passed through a central hole 192 extending through the osteotomy guide 162 at the center 166 of the arcuate configuration of the slot 164 and which is inserted into central drill hole 134, and by anchoring pin 116 which extends through a cannula 70 inserted into an opening 182, with the arcuate slot 164 juxtaposed with the series 150 of drill holes 110 in the proximal tibia 102, as seen in FIG. 11.

Figures 12, 13:
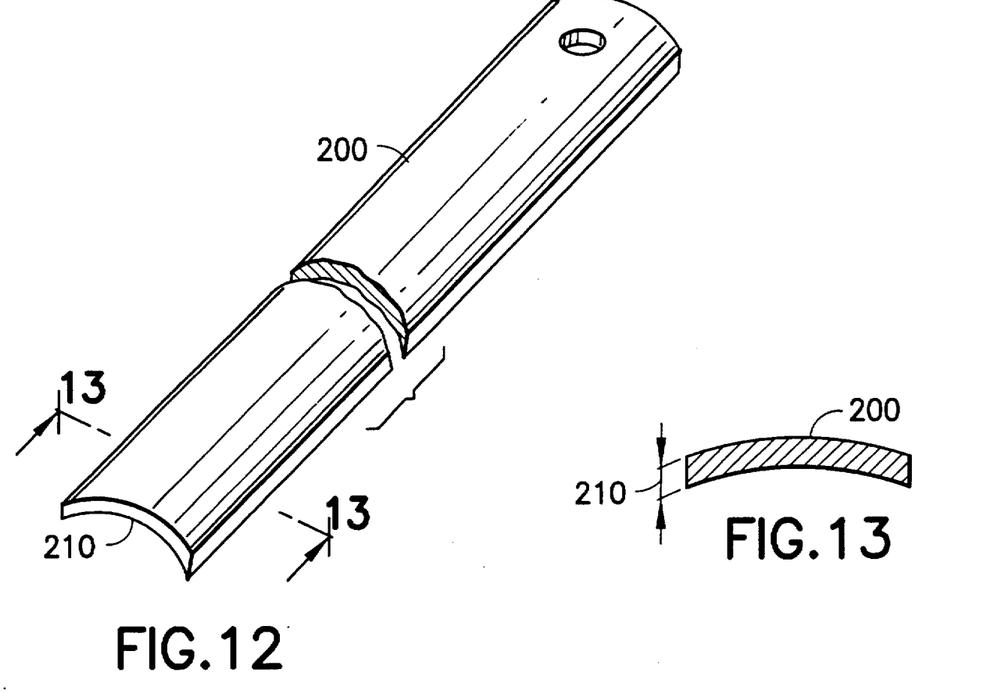
FIG. 12 is a perspective view of an osteotome constructed in accordance with the present invention.
FIG. 13 is an enlarged cross-sectional view taken along line 13—13 of FIG. 12.
Figure 14:
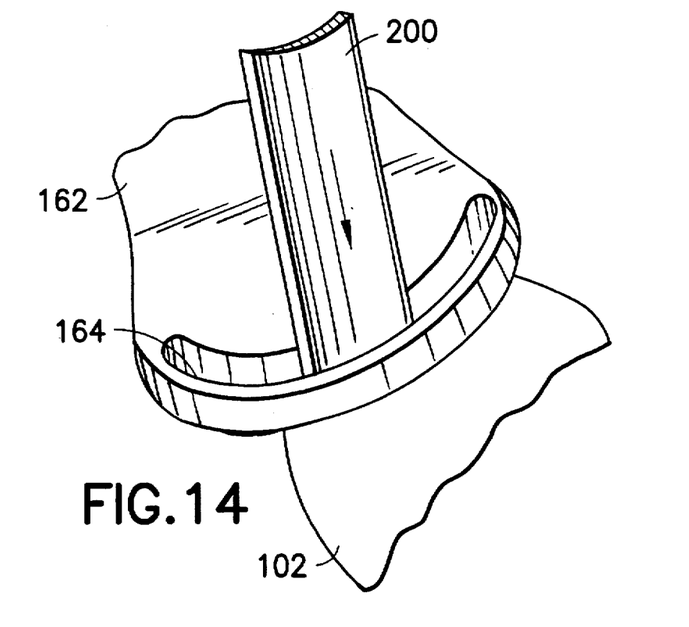
FIG. 14 is a pictorial perspective view showing the osteotome of FIG. 12 in use.

Once the osteotome guide 162 is secured in place, osteotomes are guided by the arcuate slot 164 to create the full semi-cylindrical surface contour configuration of the dome osteotomy. Thus, as illustrated in FIGS. 12 through 14, a first osteotome 200 has a curved lateral cross-sectional configuration essentially complementary to the arc of the arcuate slot 164 of the osteotome guide 162 and includes a longitudinal length and a thickness 210 enabling the osteotome 200 to be received in the slot 164 and to be guided along a curve corresponding precisely to the profile configuration of the dome osteotomy. A cutting edge 210 along the lower end of the osteotome 200 accomplishes precise shaping of the contour configuration of the dome osteotomy. A series of osteotomes constructed as illustrated by osteotome 200 are made available for the progressive creation of the semi-cylindrical surface contour configuration of the dome osteotomy, with the osteotomes progressing posteriorly through the bone of the proximal tibia 102. Preferably, the width W of the slot 164 is about twice the thickness 210 of each osteotome so that the osteotomes are manipulated relatively freely within slot 164, with the slot 164 serving as a visual guide to the surgeon. As with the drill guide 62, the position of slot 164 is shifted readily, along the arc followed by slot 164, if deemed desirable, by rotating the osteotome guide 162 about central pin 190.

Figure 15:
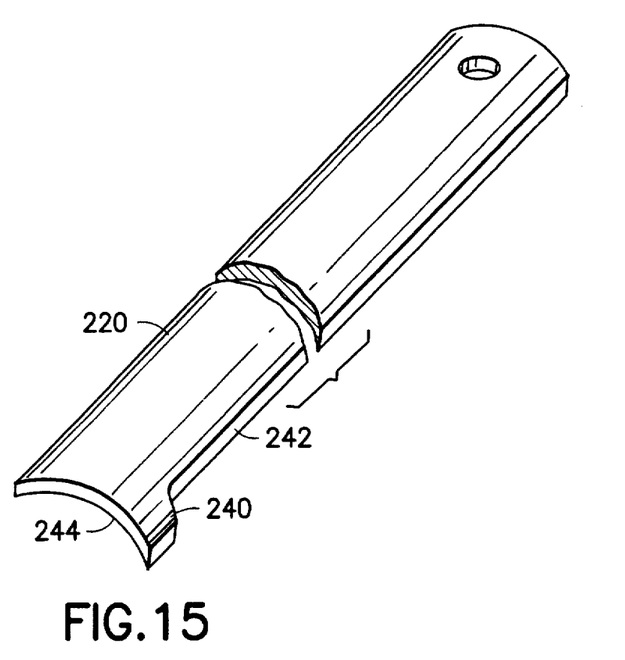
FIG. 15 is a perspective view of another osteotome constructed in accordance with the present invention.
Figure 16:
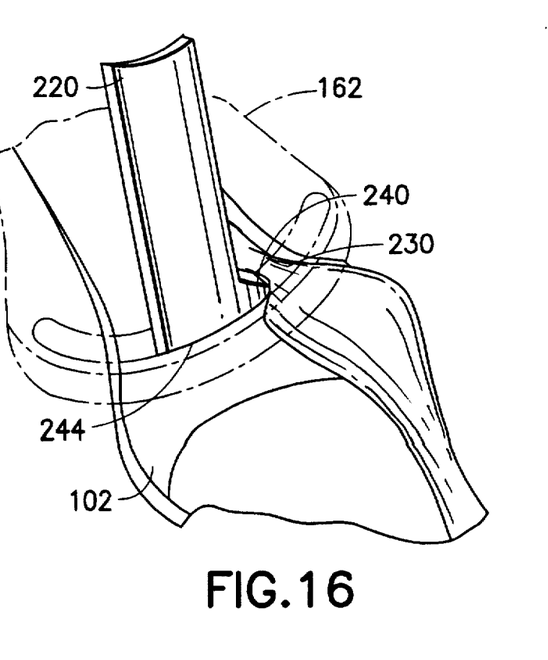
FIG. 16 is a pictorial perspective view illustrating use of the osteotome of FIG. 15.

Turning now to FIG. 15, a footed osteotome 220 is provided to assist in reaching the bone of the proximal tibia 102 lying behind the patellar tendon, illustrated at 230 with a portion broken away for purposes of illustration. Osteotome 220 extends longitudinally, also has a curved lateral cross-sectional configuration which follows the profile configuration of the semi-cylindrical surface contour configuration of the dome osteotomy and further includes a foot 240 extending laterally from the shank 242 of osteotome 220, at the cutting edge 244 of the osteotome 220. As seen in FIG. 16, wherein the osteotome guide 162 is shown in phantom for the purpose of clarifying the illustration, the foot 240 enables the cutting edge 244 to extend behind the patellar tendon 230 with minimal disturbance of the patellar tendon 230 so as to complete the full and accurate semi-cylindrical surface contour of the dome osteotomy. Both left-footed and right-footed osteotomes are provided to facilitate completion of the dome osteotomy.

Various methods have been proposed for creating a dome osteotomy. Among these methods are the use of a semicircular saw, a variety of drills and drill guides, and simply using osteotomes alone to create a "freehand" dome osteotomy. The present invention utilizes a combination of a relatively simple drill guide with cannulas to attain an accurate placement and alignment of the series 150 of drill holes 110 which series then serves as a guide for curved osteotomes 200 and 220 which create a desired dome osteotomy with exceptional accuracy. Since power saws are not used, the dome of the osteotomy is created slowly and progressively with maximum safety and minimum bone loss.

Correction is accomplished in a manner similar to that described above in connection with FIGS. 4 and 5. Such correction is relatively simple and straightforward. No angles need be measured, nor is there any necessity for meticulous calculations prior to the procedure, since correction is based upon alignment with the axis which extends from the hip to the ankle. In practice, a wire is centered over the hip and ankle and is used to indicate the axis as the axis is observed, intraoperatively, to cross the knee. In the illustrated embodiment, valgus correction progresses until the axis crosses just lateral to the lateral flare of the tibial articular surface. The ability of the surgeon to observe and adjust during the procedure enables the attainment of accuracy with ease and reliability.

It will be apparent that the present invention attains the several objects and advantages summarized above, namely: Facilitates the accurate creation of a dome osteotomy in a proximal tibia osteotomy for the correction of knee misalignment; assures accuracy in the location and orientation of the dome, as well as in the contour of the dome itself; enables correction of knee misalignment with minimal bone loss in a high tibia osteotomy; allows intraoperative adjustments to attain accurate corrections in accordance with the judgment of the surgeon during the procedure; enables varus or valgus corrections; simplifies the procedure for attaining an accurate dome configuration and orientation; provides increased control for creating a more precise and reliable osteotomy with relative ease and with greater safety; enables the creation of a reliable dome osteotomy more quickly, thereby shortening the duration of the procedure; allows the accomplishment of a precise high tibia osteotomy utilizing an anterior incision and minimal invasiveness; promotes early and reliable healing; provides a reliable alternative to total knee replacement without adversely affecting the ability of the site to receive a total knee replacement, should such a replacement become necessary in the future; reduces the chances for complications experienced in connection with corrections attempted by employing a wedge osteotomy; provides instruments of simplified construction capable of ready use with procedures of minimal complexity for the attainment of exemplary results.

It is to be understood that the above detailed description of preferred embodiments of the invention are presented by way of example only. Various details of design, construction and procedure may be modified without departing from the true spirit and scope of the invention, as set forth in the appended claims.

The embodiment of the invention in which an exclusion property or privilege is claimed are defined as follows:

1. An instrument system for creating a dome osteotomy at a selected location on a proximal tibia, the dome osteotomy having a semi-cylindrical surface contour configuration with an arcuate profile configuration placed at the selected location, the instrument system comprising:

a first guide component having a longitudinal length, a lateral width, an altitudinal thickness, and a plurality of apertures extending altitudinally through the first guide component and placed along an arc which follows the arcuate profile configuration of the dome osteotomy, the apertures being aligned essentially parallel to one another and including corresponding central axes extending altitudinally, essentially parallel to one another;

a plurality of cannulas, each cannula of the plurality of cannulas having a length greater than the altitudinal thickness of the first guide component, an inside guide surface for receiving a complementary drill and an outside guide surface complementary to a corresponding one of the plurality of apertures for being received within the one aperture for guiding the complementary drill along a drill path aligned with the corresponding central axis of the one aperture; and a first guide component affixation arrangement for affixing the first guide component to the proximal tibia with the arc of the plurality of apertures placed in juxtaposition with the selected location of the arcuate profile configuration;

the length of each cannula being great enough to assure that each drill path is located in an array of essentially parallel drill paths, with the array creating a pattern for the surface contour configuration of the dome osteotomy located at the selected location on the proximal tibia.

2. The instrument system of claim 1 wherein the guide component includes a plate-type member having a first end and a second end longitudinally opposite the first end, and the plurality of apertures are adjacent the first end.

3. The instrument system of claim 2 wherein the first guide component includes an arm extending longitudinally adjacent the second end for facilitating alignment of the plate-type member along the proximal tibia.

4. The instrument system of claim 3 including:

at least one opening located in the arm, the opening extending altitudinally through the arm and having a central axis essentially parallel to the central axes of the plurality of apertures adjacent the first end of the plate-type member; and at least one further cannula having a length greater than the altitudinal thickness of the first guide component, a further inside guide surface, and a further outside guide surface complementary to the opening.

5. The instrument system of claim 4 wherein the arc along which the apertures are placed includes a center located between the first and second ends of the plate-type member, and the affixation arrangement includes a hole passing altitudinally through the plate-type member at the center of the arc.

6. The instrument system of claim 1 including:

a second guide component having a longitudinal length, a lateral width, an altitudinal thickness, and a slot extending along an arc which follows the arcuate profile configuration of the dome osteotomy, the slot extending altitudinally through the second guide component;

a second guide component affixation arrangement for affixing the second guide component to the proximal tibia with the arc of the slot juxtaposed with the selected location of the arcuate profile configuration; and at least one osteotome having a longitudinal length greater than the altitudinal thickness of the second guide component for extending altitudinally through the slot, the osteotome having a lateral curved configuration complementary to the arc of the slot for reception within the slot, and a cutting edge extending along the lateral curved configuration for creating the semi-cylindrical surface contour configuration of the dome osteotomy along the arcuate profile configuration as the osteotome is guided by the slot.

7. The instrument system of claim 6 wherein the arc along which the slot extends includes a center located on the second guide component, and the second guide affixation arrangement includes a hole extending altitudinal through the second guide component at the center of the arc along which the slot extends.

8. The instrument system of claim 6 wherein the osteotome includes a shank extending along the longitudinal length of the osteotome, and a foot extending laterally from the shank at the cutting edge.

9. An osteotome for use in an instrument system for creating a dome osteotomy at a selected location on a proximal tibia, the dome osteotomy having a semi-cylindrical surface contour configuration with an arcuate profile configuration placed at the selected location, the instrument system including a guide component having a slot extending along an arc which follows the arcuate profile configuration of the dome osteotomy, the osteotome having:

a longitudinal length for extending through the slot;

a lateral curved configuration complementary to the arc of the slot for reception within the slot; and a cutting edge extending along the lateral curved configuration for creating the semi-cylindrical surface contour configuration of the dome osteotomy along the arcuate profile configuration as the osteotome is guided by the slot.

10. The osteotome of claim 9 wherein the osteotome includes a shank extending along the longitudinal length of the osteotome, and a foot extending laterally from the shank at the cutting edge.

11. An improvement in a method for creating a dome osteotomy at a selected location on a proximal tibia, the dome osteotomy having a semi-cylindrical surface contour configuration with an arcuate profile configuration placed at the selected location, the improvement comprising the steps of:

placing a first guide component on the tibia, the first guide component having an altitudinal thickness and a plurality of apertures extending altitudinally through the first guide component and placed along an arc which follows the arcuate profile configuration of the dome osteotomy, the apertures being aligned essentially parallel to one another and including corresponding central axes extending altitudinally, essentially parallel to one another;

locating the first guide component so as to juxtapose the arc of the plurality of apertures with the location of the arcuate profile configuration of the dome osteotomy;

placing a cannula in each of the plurality of apertures, the cannula having a length greater than the altitudinal thickness of the first guide component, an inside guide surface for receiving a complementary drill and an outside guide surface complementary to a corresponding one of the plurality of apertures for being received within the one aperture for guiding the complementary drill along a drill path aligned with the corresponding central axis of the one aperture; and guiding a complementary drill along each inside guide surface to establish an array of essentially parallel drill holes in the tibia, the array creating a pattern for the surface contour configuration of the dome osteotomy located at the selected location on the proximal tibia.

12. The method of claim 11 including the steps of:

placing a second guide component on the tibia in juxtaposition with the array of drill holes, the second guide component having a slot which follows the arcuate profile configuration of the dome osteotomy;

registering the slot with the array of drill holes;

advancing at least one osteotome through the slot and into the tibia to create the dome osteotomy, the osteotome being guided by the slot to establish the surface contour configuration of the dome osteotomy.

13. The method of claim 12 wherein the osteotome has a lateral curved configuration which follows the arcuate profile configuration of the dome osteotomy such that advancement of the osteotome through the slot establishes at least a portion of the surface contour configuration of the dome osteotomy.

* * * * *